US009075021B2

(12) United States Patent
Quetua

(10) Patent No.: US 9,075,021 B2
(45) Date of Patent: Jul. 7, 2015

(54) METHODS AND SYSTEMS FOR MONITORING CONTENT OF COATING SOLUTIONS USING AUTOMATED TITRATION DEVICES

(75) Inventor: Renato Manahan Quetua, Vancouver (CA)

(73) Assignee: Toyota Motor Engineering & Manufacturing North America, Inc., Erlanger, KY (US)

( * ) Notice: Subject to any disclaimer, the term of this patent is extended or adjusted under 35 U.S.C. 154(b) by 454 days.

(21) Appl. No.: 13/398,978

(22) Filed: Feb. 17, 2012

(65) Prior Publication Data
US 2013/0217134 A1  Aug. 22, 2013

(51) Int. Cl.
  G01N 21/79  (2006.01)
  G01N 31/16  (2006.01)
(52) U.S. Cl.
  CPC .............. *G01N 21/79* (2013.01); *Y10T 436/12* (2015.01); *G01N 31/16* (2013.01)
(58) Field of Classification Search
  CPC ....... G01N 21/79; G01N 31/16; Y10T 436/12
  USPC .............................................. 436/163, 51, 12
  See application file for complete search history.

(56) References Cited

U.S. PATENT DOCUMENTS

| 4,504,324 | A | * | 3/1985 | Furuno ........................ 148/255 |
| 4,950,610 | A | | 8/1990 | Tittle |
| 5,192,509 | A | | 3/1993 | Surjaatmadja et al. |
| 5,618,495 | A | * | 4/1997 | Mount et al. ............... 422/82.05 |
| 5,640,330 | A | | 6/1997 | Cooper et al. |
| 5,834,319 | A | | 11/1998 | Ekins |
| 7,057,156 | B2 | | 6/2006 | Coates et al. |
| 7,349,760 | B2 | * | 3/2008 | Wei et al. ....................... 700/267 |
| 7,747,072 | B2 | | 6/2010 | Yoshiura et al. |
| 2007/0231910 | A1 | | 10/2007 | DeGrandpre et al. |
| 2008/0003140 | A1 | | 1/2008 | Di et al. |
| 2008/0219891 | A1 | | 9/2008 | McDevitt et al. |
| 2009/0275144 | A1 | | 11/2009 | Petersson |
| 2010/0135853 | A1 | | 6/2010 | Broga et al. |
| 2010/0210026 | A1 | | 8/2010 | Hintz et al. |
| 2010/0238968 | A1 | | 9/2010 | Plotnikov et al. |
| 2011/0222743 | A1 | | 9/2011 | Tanaka et al. |

OTHER PUBLICATIONS http://enterprise.astm.org/filtrexx40.cgi?+REDLINE_PAGES/B368.htm.*
Edvaldo da Nobrega Gaiao, Valdomiro Lacerda Martins, Wellington da Silva Lyra, Luciano Farias de Almeida, Edvan Cirino da Silva, Mario Cesar Ugulino Araujo, Digital image-based titrations, Analytica Chimica Acta, vol. 570 (2006) 283-290.*
Wasin Wongwilai, Somchai Lapanantnoppakhun, Supara Grudpan, Kate Grudpan "Webcam camera as a detector for a simple lab-on-chip time based approach" Talanta 81 (2010) 1137-1141.*

* cited by examiner

*Primary Examiner* — Christopher A. Hixson
*Assistant Examiner* — Emily Berkeley
(74) *Attorney, Agent, or Firm* — Dinsmore & Shohl LLP

(57) ABSTRACT

A method for monitoring content of a coating solution for coating components includes supplying a tank with the coating solution containing a concentration of a solvent and a concentration of a coating material. The concentration of the coating material is tested using a titration process. The titration process may include controllably contacting a volume of the coating solution with a reagent solution to form a mixture and using a color processing device to obtain input color data of the mixture to detect an end-point of the titration process. One or both of the solvent and the coating material is supplied to the tank based on an amount of coating solution contacted with the reagent solution when the color processing device detects an input color data signaling the end-point of the titration process.

16 Claims, 5 Drawing Sheets

METHODS AND SYSTEMS FOR MONITORING CONTENT OF COATING SOLUTIONS USING AUTOMATED TITRATION DEVICES

TECHNICAL FIELD

The present specification generally relates to methods and systems for monitoring content of coating solutions, and particularly, to methods and systems for determining a concentration of a chemical in a solution using automated titration in an industrial environment.

BACKGROUND

Titration is used for determining a concentration of a constituent of a solution or for determining a characteristic of a solution. In some titrations, acidity or alkalinity is determined by adding an acid or base to a solution containing an indicator. When the pH reaches a particular value, the color of the indicator changes. For example, a common indicator is phenolpthalein which is colorless in acidic solutions, but is red in solutions having a pH exceeding nine. Other indicators are available for responding to the presence of particular ions in solution. For example, permanganate ions respond to the presence of iron or nitrite ions in solution. A characteristic of a solution of unknown concentration (the analyte) containing an indicator may be determined from the quantity of a titrant of known concentration added to the solution to bring about a change in indicator color. Alternatively, a reverse or back titration may be performed, where the titrant is a solution of unknown concentration (the analyte), and a solution of known concentration is used as the titrand.

Titrations are conveniently carried out in a laboratory environment with a relatively inexpensive apparatus since conditions can be easily controlled. However, in manufacturing operations where conditions are not so easily controlled, use of titration to test or analyze and thereby control the characteristics of various chemical baths is more difficult and expensive. In some situations, analytical techniques other than titration are employed to monitor characteristics of solutions, including spectroscopy techniques that require an expensive and complex apparatus.

Employment of titration as a process control technique is difficult, as human error is introduced when technicians must judge the change in color of the indicator at the end-point of the titration. Furthermore, continuity in judging the titration end-point is jeopardized when multiple technicians run titrations over time. Accordingly, there is a need for an automated, inexpensive titration apparatus for use in process control that can automatically determine the end-point of a titration reaction in an industrial setting.

SUMMARY

In one embodiment, a method for monitoring content of a coating solution for coating components includes supplying a tank with the coating solution containing a concentration of a solvent and a concentration of a coating material. The concentration of the coating material is tested using a titration process. The titration process may include controllably contacting a volume of the coating solution with a reagent solution to form a mixture and using a color processing device to obtain input color data of the mixture to detect an end-point of the titration process. One or both of the solvent and the coating material is supplied to the tank based on an amount of coating solution contacted with the reagent solution when the color processing device detects an input color data signaling the end-point of the titration process.

In another embodiment, a method for monitoring content of a coating solution for in-line coating of components includes supplying a tank with the coating solution containing a concentration of a solvent and a concentration of a coating material. The concentration of the coating material is tested using a titration process. The titration process includes acquiring a sample of the coating solution from the tank and locating the sample of the coating solution in a dispenser. The sample of the coating solution is controllably dispensed from the dispenser into a container holding a measured amount of a reagent solution using an actuator operably connected to the dispenser. Input color data is obtained from a color processing device monitoring the reagent solution with the coating solution added thereto. The input color data is compared with threshold color data. The method for monitoring content of a coating solution for in-line coating of components may additionally include supplying one or both of the solvent and the coating material to the tank based, at least in part, on comparing the input color data with the threshold color data saved in memory.

In yet another embodiment, a method for monitoring content of a coating solution for coating components is provided. The method includes maintaining a coating solution comprising a concentration of a solvent and a concentration of a coating material supplied to a tank by testing the concentration of the coating material using a titration process, wherein the titration process comprises controllably contacting a volume of the coating solution with a reagent solution to form a mixture and using a color processing device to obtain input color data of the mixture to detect an end-point of the titration process. One or both of the solvent and the coating material is supplied to the tank based on the amount of coating solution contacted with the reagent solution when the end-point of the titration process is detected.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Embodiments described herein generally relate to methods and systems for monitoring content of coating solutions used to coat components during an assembly process, such as automotive components of an in-line assembly process. The systems and methods may utilize an automated titration device that includes a color processing device that monitors the color change of an indicator throughout a titration. Utilizing the color processing device, the automated titration device may determine a titration end-point based on color data received by the color processing device. From the volume or amount of titrant contacted with titrand at the titration end-point, chemical characteristics of an analyte, such as a coating solution, may be determined.

As used herein, the term "titrant" refers to a reactant solution that is measurably dispensed over the time of the titration into a titrand. As used herein, the term "titrand" refers to the reactant solution that has a pre-measured volume and into which the titrant is measurably dispensed over the time of the titration. As used herein, the term "analyte" refers to a chemical solution which has unknown properties and is undergoing analysis. As used herein, the term "indicator" refers to a chemical that changes visible color when the reactants of the titrant and titrand reach a specific stochiometric ratio.

Figure 1:
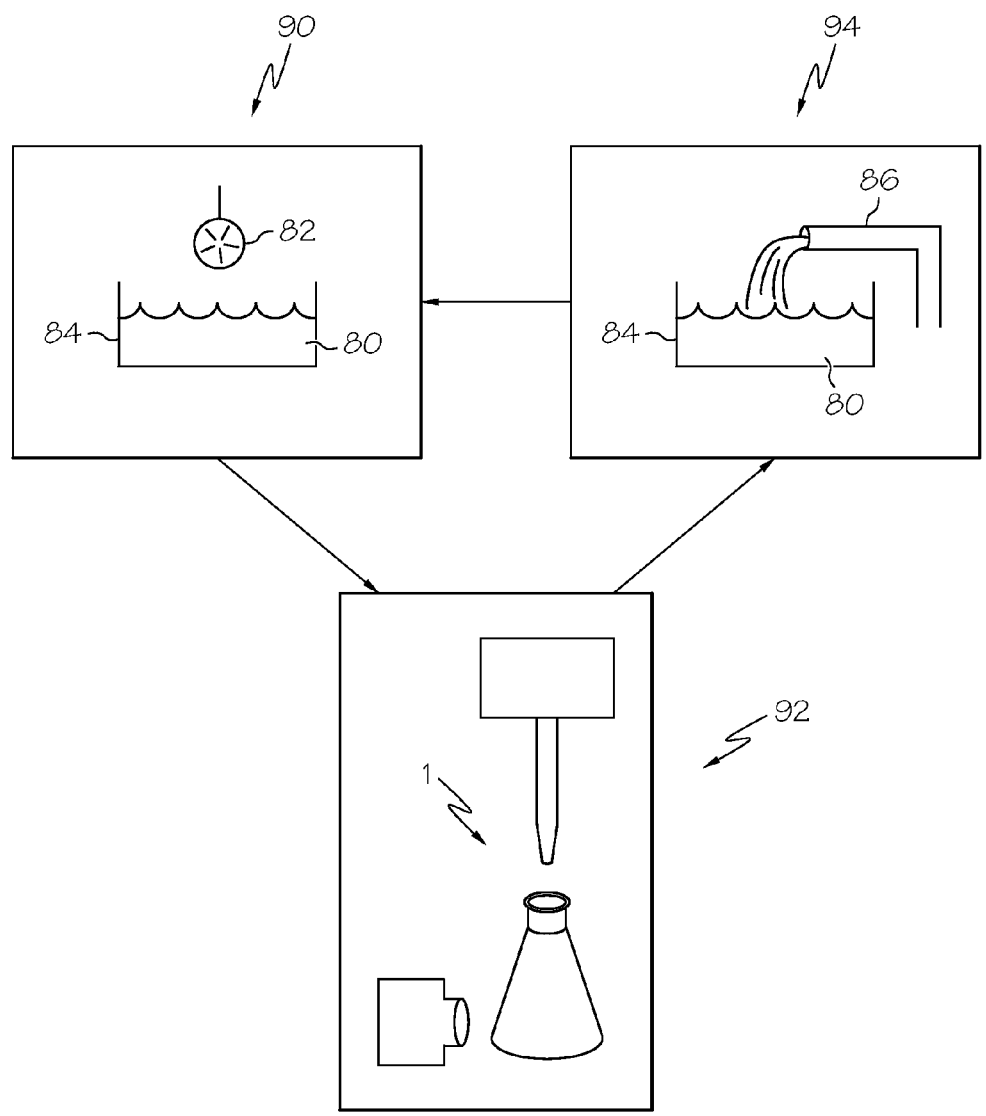
FIG. 1 depicts a schematic diagram of a system for monitoring content of a coating solution, according to one or more embodiments shown and described herein.

FIG. 1 shows a schematic diagram of a system for monitoring the content of a coating solution for coating components. The system includes a coating station 90, a chemical analysis station 92, and a chemical modification station 94. At the coating station 90, a coating solution 80 is used to coat a mechanical component 82, such as a component that is used in an assembly process. For example, an aluminum wheel for an automobile may be coated with a coating solution 80 containing a conversion coating material at the coating station 90. The coating may occur by submerging the component 82, such as the aluminum wheel, into a tank 84 containing the coating solution 80 that contains the conversion coating material. Alternatively, the coating may occur by a spray process or any other suitable coating process.

The coating process at the coating station 90 may beneficially alter the surface properties of the component 82. The coating solution 80 may comprise at least a solvent and a coating material. In one embodiment, the coating material is a conversion coating material. A conversion coating material may improve corrosion resistance of a metal component 82, such as an aluminum wheel. Coating materials are commercially available, such as the conversion coating material ALODINE® 4595 (available from Henkel AG & Co. KGaA, Dusseldorf, Germany). The solvent contained in the coating solution 80 may be water, in some embodiments de-ionized water (DIW), or any other suitable solvent such as an organic solvent.

The coating material may be mixed with the solvent in a tank 84 to produce a coating solution 80, such that a desired concentration of coating material is present in the coating solution 80. In one embodiment, the coating solution 80 may comprise between about 0.5% vol. and about 10% vol. conversion coating material. In another embodiment, the coating solution 80 may comprise between about 1% vol. and about 6% vol. conversion coating material.

The components 82 that are coated at the coating station 90 may undergo other processes prior to or following the coating step at the coating station 90. For example, the component 82 may undergo one or more cleanings prior to and/or following the coating step. In some embodiments, the components 82 may undergo multiple coating steps, including coating steps utilizing different coatings, or multiple coating steps utilizing the same coating. In one embodiment, the component 82, such as an aluminum automobile wheel, may undergo a de-greasing process prior to the coating process at coating station 90. In a de-greasing process, the aluminum wheel may be cleaned of at least some residual dirt and oil present on the surface of the aluminum wheel. The aluminum wheel may be contacted with water or other organic compounds and optionally contacted with a cleansing agent. The contacting may be a liquid rinse or submersion of the aluminum wheel in a liquid. In one embodiment, the degreasing process includes contacting the aluminum wheel with a solution containing a commercially available cleansing agent, such as RIDOLINE® 212 (available from Henkel AG & Co. KGaA, Dusseldorf, Germany). However, other cleaning agents may be suitable as a de-greasing agent for this process.

In one embodiment, the component 82, such as an aluminum wheel, undergoes an acid rinse or acid bath, wherein the aluminum wheel is contacted with an acid. In an acid bath or rinse, the component 82 is contacted with an acidic solution which may etch the surface of the aluminum wheel. Contacting the aluminum wheel with an acid may deoxidize the surface of the aluminum wheel, which may be beneficial for the coating process at coating station 90, such as a conversion coating process.

Still referring to FIG. 1, the coating solution 80 of the coating station 90 may be housed in the tank 84 and be monitored periodically. The chemical analysis station 92 may be used to analyze the chemical properties and/or composition of the coating solution 80 used at the coating station 90. In one embodiment, the coating material concentration of the coating solution 80 is analyzed periodically such as every eight hours. However, the contents of the coating solution 80 may be checked less than or more than every eight hours, such as every 1, 2, 3, 4, 5, 6, 7, 9, 10, 12, 14, 16, 18, 20, 22.1 of 24 hours. The contents may be checked even less periodically, such as every 2, 3, 4, 7, 30or 60 days. The contents may alternatively be checked more frequently than each hour. The contents may be checked on a non regular schedule, where the time intervals between coating solution 80 analyses are not consistent.

At the chemical analysis station 92, the coating solution 80 used to coat the components 82 at the coating station 90 is analyzed. Any property of the coating solution 80 may be analyzed, including its chemical composition such as a chemical concentration of a chemical in the coating solution 80. For example, the chemical concentration of the coating material in the coating solution 80 containing coating material and solvent may be tested and determined. In one embodiment, the analysis is performed with a titration procedure using an automated titration device 1. Embodiments of the automated titration device 1 will be further described in detail herein. In one embodiment, the concentration of the conversion coating material in the coating solution 80 containing conversion coating material and the solvent, DIW, is analyzed at the chemical analysis station 92 using the automated titration device 1.

Following the analysis of the coating solution 80 at the chemical analysis station 92, the chemical properties of the coating solution 80 may be modified at the chemical modification station 94. For example, the coating solution 80 containing the conversion coating material and the solvent may be chemically modified by the addition of a volume of the conversion coating material or a volume of the solvent. Alternatively, both of the conversion coating material and solvent may be added, for example if the volume of coating solution 80 in the tank 84 of the coating station 90 is low. A volume of the coating solution 80 may be removed from the tank 84, and optionally, a volume of the conversion coating material, solvent, or both, may be added to the coating solution 80 in the tank 84. The addition of any component into the coating solution 80 may be controlled by a pump device 86, which can pump liquid chemical components into the tank 84 to be mixed with the coating solution 80. The addition of components to the tank 84 may be manual, such as the addition of a liquid component by an operator.

The information generated from the chemical analysis station 92 is used to determine if the coating solution 80 used for coating components 82 at the coating station 90 should be modified at the chemical modification station 94. For example, the analysis at the chemical analysis station 92 may report that the concentration of conversion coating material is less than a desired concentration that is optimal for component 82 coating. If the conversion coating concentration is too low, a volume of conversion coating material may be added to the tank 84 with the pump device 86. Alternatively, if the conversion coating concentration is too high, a volume of solvent may be added to the tank 84. If the tank 84 needs to be replenished with coating solution 80, both conversion coating material and solvent, in desired proportions, can be added to the tank 84.

Monitoring the contents of the coating solution 80 at chemical analysis station 92 and modifying the chemical properties of the coating solution 80 at the chemical modification station 94 may be beneficial to the coating process of coating station 90. In one embodiment, if the conversion coating material concentration of the coating solution 80 is too low or too high, the conversion coating material may not be properly coated onto a component 82 and the component 82 may have poor resistance to corrosion as compared with a component 82 coated with a coating solution 80 of the desired concentration of conversion coating material.

Figure 2:
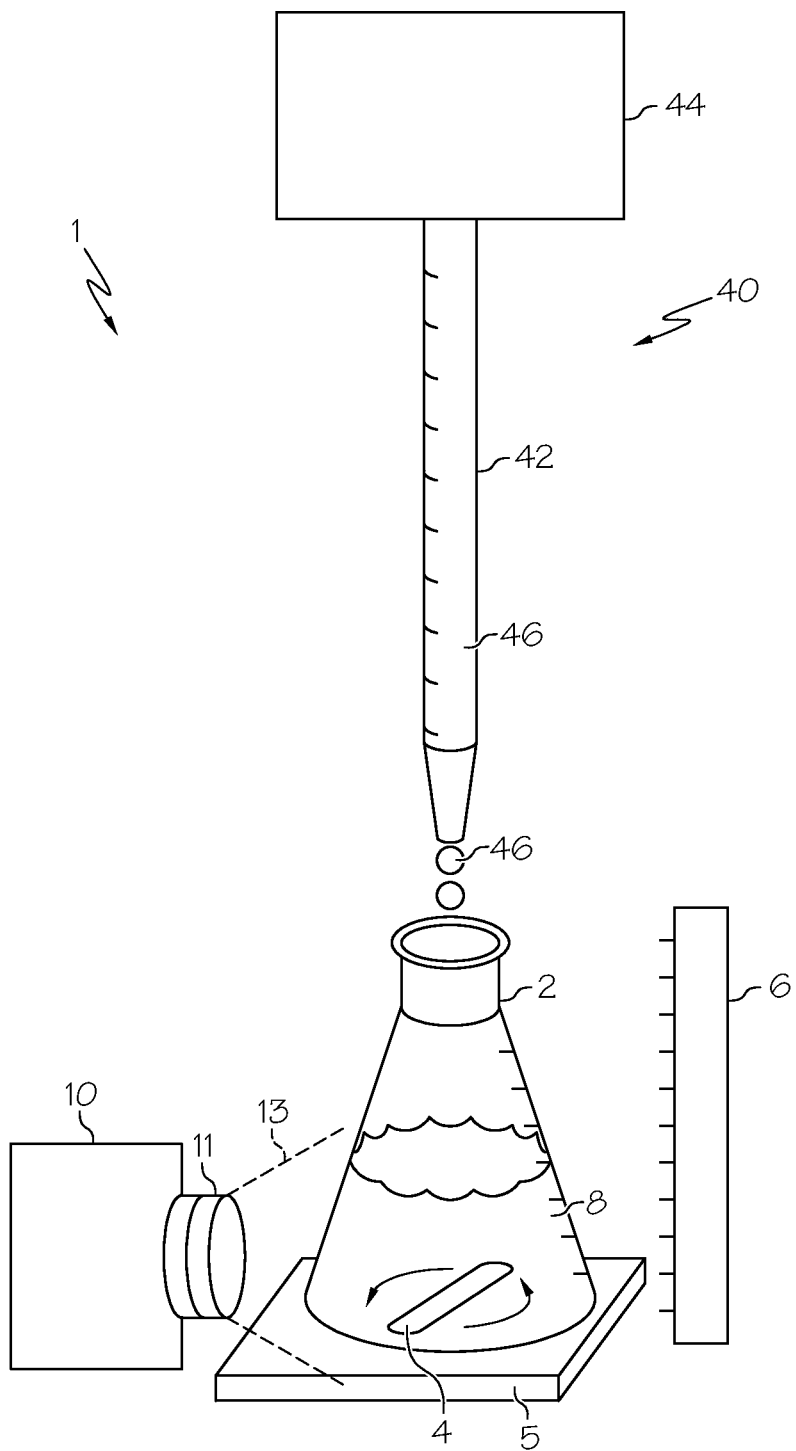
FIG. 2 depicts an automated titration device, according to one or more embodiments shown and described herein.
Figure 3:
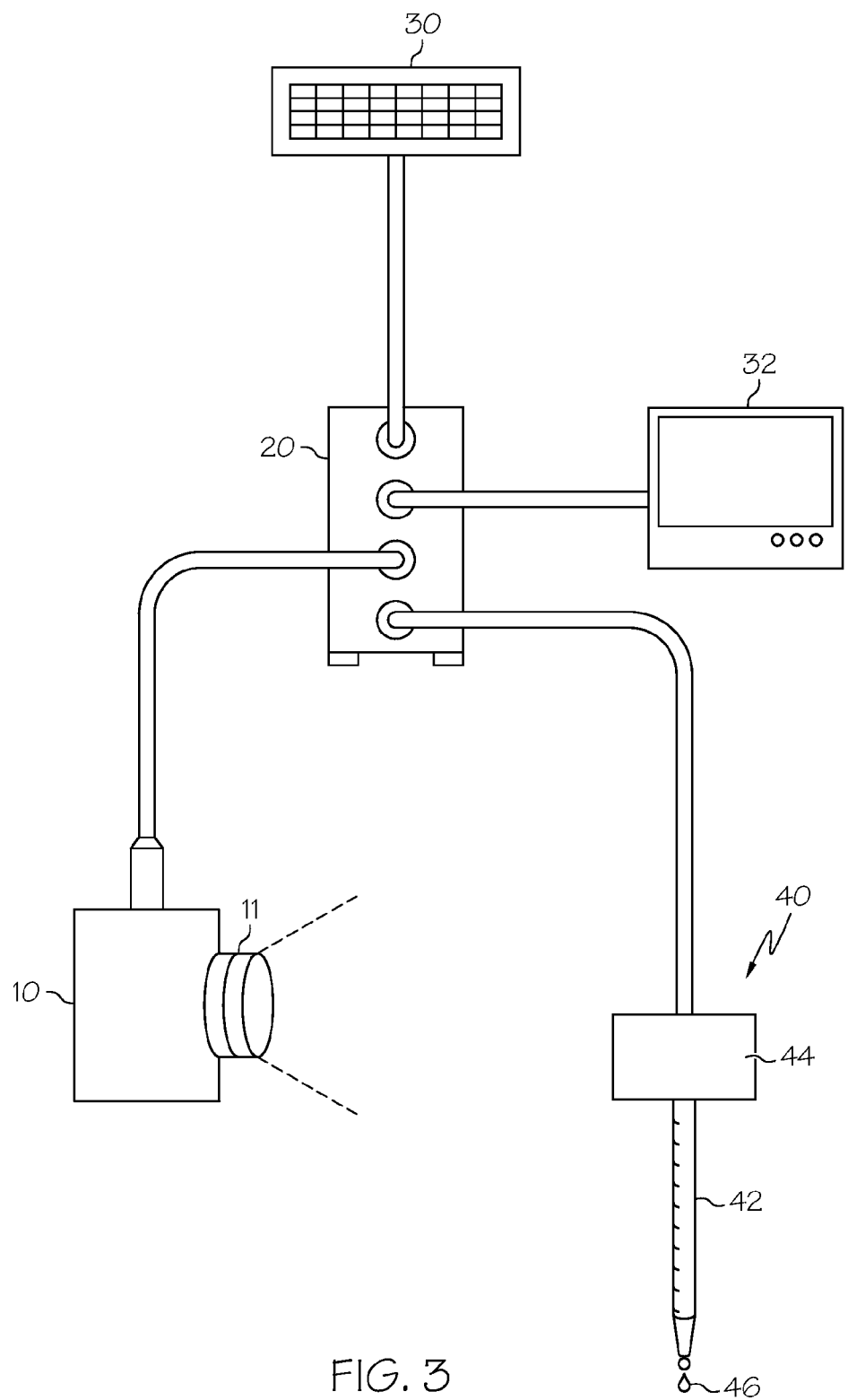
FIG. 3 depicts a schematic diagram of the electrical components of the automated titration device of FIG. 2, according to one or more embodiments shown and described herein.

Referring now to FIG. 1-3, embodiments of the automated titration device 1 are shown. Such an automated titration device 1 may be utilized in the chemical analysis station 92 to determine the chemical composition of the coating solution 80 used in the coating station 90. The automated titration device 1 includes a container 2 that may be transparent and a dispenser 40. The container 2 is positioned under the dispenser 40 to be capable of receiving a titrant 46 from the dispenser 40. The container 2 may be a glass Erlenmeyer flask, a glass jar, or any transparent or suitable translucent container. The container 2 is at least partially filled with a measured amount of titrand 8 prior to the start of the titration process. The dispenser 40 comprises a pipette 42 and an actuator 44. The titrant 46 is positioned inside of the pipette 42 prior to the start of the titration process. The container 2 sits on a magnetic stirring rod base 5 and has a magnetic stirring rod 4 positioned therein. The magnetic stifling rod base 5 can rotate the magnetic stifling rod 4 that is located within container 2 to mix the solution within container 2 during the titration process.

A color processing device 10 is positioned beside the container 2 with a color input region 11 facing the container 2. The color processing device 10 may include a color input region 11 which may include a lens. The color processing device 10 may optionally include a lighting system (represented by dotted lines 13) having a light source which shines onto the sample to be analyzed. In one embodiment, the color processing device 10 is capable of measuring the color of a sample chemical solution in its view and may be able to extract RGB color data from a given sample. RGB color data represents colors using an RGB color model, which is an additive color model in which red, green, and blue light is added together in various ways to reproduce a broad array of colors. The RGB color model has three additive colors: red, blue, and green, which are added in varying proportion to produce representation of color which can be stored or generated as RGB color data. A color may be quantified as RGB color data in numerous ways, including an RGB triplet, where three values representing red, green and blue respectively can vary from zero to a defined maximum value. An RGB triplet can use varying notation for each of the red, green or blue elements of the triplet, such as, but not limited to, arithmetic notation (0 to 1), percentage notation (0% to 100%), digital 8-bit per channel notation (0 to 255), and digital 16-bit per channel notation (0 to 65535). The color processing device 10 may extract other data corresponding to color models other than RGB, or may extract color data based on relative lighting, such as a grayscale or monochrome model. In one embodiment, a suitable color processing device 10 is the OMRON, Model E3X DAC11-S. In some embodiments, a mirror 6 is used to reflect light back toward the color processing device 10 and is positioned near the container 2 on the side opposite the color processing device 10, as to reflect light into the color input region 11 of the color processing device 10.

Referring now to FIG. 3, a schematic diagram of the automated titration device 1 of FIG. 2 is shown that features additional components of the automated titration device 1. A controller 20 is communicatively connected to the color processing device 10. The controller 20 may be any computer capable of executing logic stored in a memory. As used herein, the phrase "communicatively connected" means that a connection exists between two devices or components of a device capable of sending and/or receiving some electrical message or signal, or the two or more devices or components are operably connected to one another. The controller 20 is also communicatively connected to a user input interface 30 and a display 32. The user input interface 30 may comprise buttons, knobs, and the like, which can be used to input information to the controller 20. The user input interface 30 may be a keyboard and/or mouse. The display 32 is capable of receiving information from the controller 20 and visually showing an image of such information. The controller 20 may be connected to an actuator 44 of dispenser 40. The controller 20 may communicate with the actuator 44 to signal the actuator 44 to drop titrant 46 into the titrand 8 located in container 2 (FIG. 2). In some embodiments, more than one controller may be utilized by the automated titration device 1, and the controller 20 may be contained within a component of the automated titration device 1, such as the color processing device 12.

Figure 4:
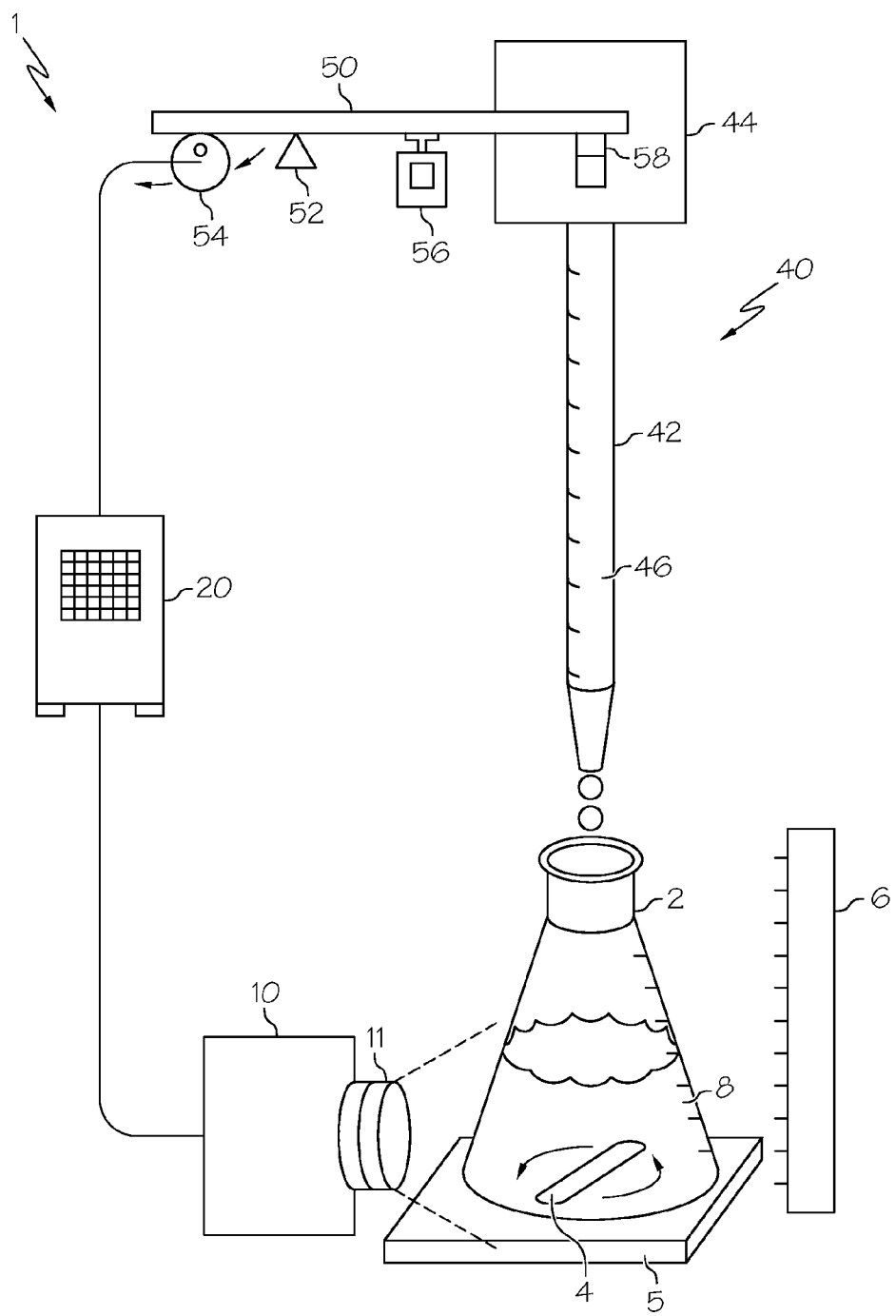
FIG. 4 depicts an automated titration device comprising a mechanical lever, according to one or more embodiments shown and described herein.

FIG. 4 shows an embodiment of the automated titration device 1 including a mechanical dispenser 40 including a lever 50 and a fulcrum 52. The dispenser 40 has an actuator 44 with a button 58. The lever 50 is mechanically connected to a counter 56, the actuator 44, and a motor 54. The counter 56 displays a number and starts at zero and displays one number higher each time it is pressed. The fulcrum 52 of the lever 50 separates the lever 50 into two sides, wherein the actuator button 58 and counter 56 may be connected to one side of the lever 50 and the motor 54 may be connected to the other side of the lever 50. The motor 54 is mechanically connected to the lever 50 and communicatively connected to controller 20. In one embodiment, the motor 54 rotates a cam which variably moves one side of the lever 50 up and down. On each upstroke of motor 54, the lever 50 presses down on the counter 56 and the button 58, causing the counter 56 to count up and causing the dispenser 40 to drop a set volume of titrant 46 into the container 2. Throughout the titration, the color processing device 10 communicates the color input data of the titrant/titrand mixture with the controller 20. At the end-point of the titration, the controller 20 communicates with the motor 54 to shut off. Therefore, at the titration end-point, the counter 56 will display how many times the button 58 on the actuator 44 has been pressed, which allows the user to determine the volume of titrant 46 dropped into container 2 at the time of the titration end-point.

In one embodiment, the titration process used to analyze the coating solution 80 at the chemical analysis station 92 may be a back titration. In a back titration, the titrant 46 includes the analyte, for example the coating solution 80, and is dropped into a titrand 8 of known concentration. The chemicals within the titrant 46 and titrand 8 react when contacted with one another. When a certain amount of titrant 46 is added, the reaction stops. At this point, the titrand 8 reactant is a limiting reagent, and has been fully consumed by reaction with a volume of the titrant 46. When the titrand 8 reactant has been fully consumed, it is said to be the end-point of the titration.

An indicator may be present in the titrant/titrand mixture that can detect the end-point of the titration and signal the end-point by changing color. The indicator may be inserted to the titrand 8 in the container 2 prior to the start of the titration process. Alternatively, the indicator may be the reactant of the titrand 8, and the reactant of the titrand 8 will change colors at the end-point of the titration. Titration processes may utilize varying reactants and corresponding indicators.

In one embodiment, a redox titration is used to determine the concentration of conversion coating material in a coating solution 80 containing conversion coating material and DIW. A redox titration is based on a reduction-oxidation reaction between an oxidizing agent and a reducing agent. Some redox titrations do not require an indicator, due to the natural color of the constituents. For instance, in permanganometry the appearance or disappearance of a pink or purple color signals the end-point of the titration because of the color of the excess oxidizing agent potassium permanganate.

Various other titration processes include an acid base titration. For example, a common indicator in an acid base titration is phenolpthalein which is colorless in acidic solutions, but is red in solutions having a pH exceeding nine. Other indicators that change colors at particular pH's are methyl orange xylene cyanol, methyl red, litmus, and bromophenol blue. In some embodiments, a forward titration procedure comprises dropping a measured volume of a titrant 46 containing a reactant of known concentration into the titrand 8. In these embodiments, the titrand 8 contains the analyte, the chemical solution of unknown concentration, and in some titrations a separate indicator.

Figure 5:
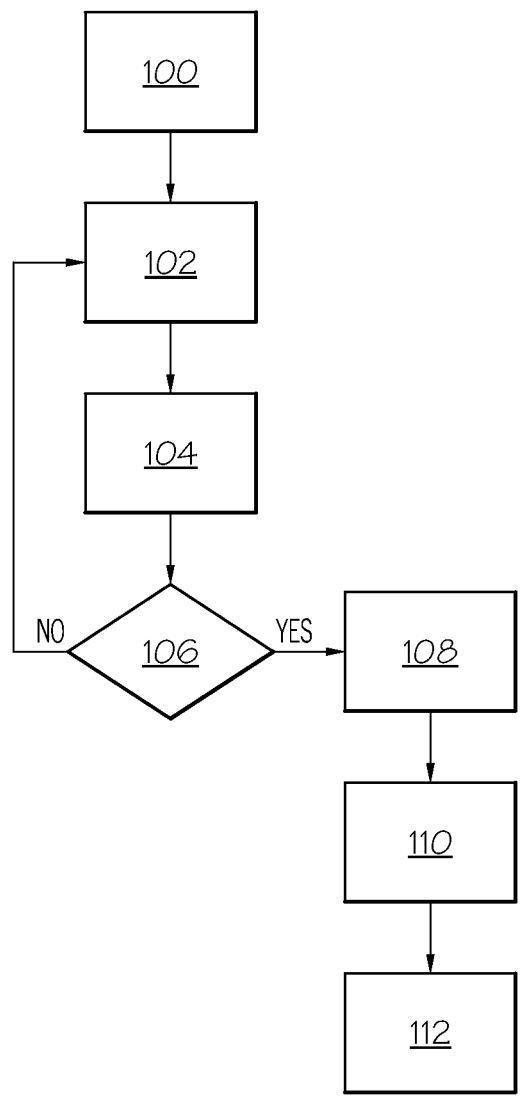
FIG. 5 depicts a schematic diagram of the process steps for monitoring the contents of a coating solution by using titration, according to one or more embodiments shown and described herein.

FIG. 5 depicts a schematic diagram of the process for monitoring the contents of the coating solution 80 using the automated titration device 1 of FIG. 2-4. The coating solution 80 may contain a concentration of conversion coating material and a concentration of a solvent. In a titration preparation step 100, the automated titration device 1 is prepared for an analysis of the concentration of conversion coating material in the coating solution 80. A surplus amount of coating solution 80 is supplied to the dispenser 40 to be used as the titrant 46. A titrand 8 is prepared and positioned in the container 2. The titrand 8 may comprise a reactant and an indicator, or a reactant that acts as an indicator. In one embodiment, the titrand 8 includes water, $KMnO_4$, and $H2SO_4$, and specifically 50 mL of water, 10 mL of 0.042N $KMnO_4$, and 5 mL of 50% $H2SO_4$.

After the titration is prepared in the titration preparation step 100, in the titrant addition step 102 a volume of the titrant 46 is contacted with the titrand 8 in the container 2 to make a titrant/titrand mixture in the container 2. The titrant 46 is added in a measured volume in this step, and continually is added throughout the titration in measured volumes. In one embodiment, to begin the titrant addition step 102, a user inputs a start command to the user input interface 30 which communicates with the controller 20 to begin the titration. During the titration process, the dispenser 40 drops measured amounts of the titrant 46 into the container 2 wherein it is mixed with the titrand 8. In one embodiment, the controller 20 communicates with the actuator 44 of the dispenser 40 to dispense a desired amount of the titrant 46 from the pipette 42, for example a desired amount of the titrant 46 per desired time unit. In one embodiment, the dispenser 40 may drop a particular volume of the titrant 46 per minute at a constant volumetric rate per second. In another embodiment, the dispenser 40 may drop a selected volume of titrant 46 each time the controller 20 communicates to the actuator 44 to drop that selected volume of titrant 46.

After each amount of titrant 46 is contacted with the titrand 8 in the titrant addition step 102, a color sensing step 104 occurs wherein the color processing device 10 senses the color of the titrant/titrand mixture in the container 2. The color processing device 10 receives the color of the titrant/titrand mixture and interprets the input color of the titrant/titrand mixture into input color data based on an RGB scale. The input color data is then communicated to the controller 20. The color sensing step 104 is performed continuously through the titration process, or alternatively after each new addition or a number of additions of titrant 46 from the dispenser 40.

Following the color sensing step 104, the end-point determination step 106 determines if the titration has reached its end-point. The controller 20 is supplied with threshold color data and compares the input color data and threshold color data to determine if the titration reaction has reached its end-point. The controller 20 is supplied with threshold color data. The threshold color data may be determined by previously performed titration reactions which have been calibrated with a titrant 46 and titrand 8 of known reactant concentration. The controller 20 compares the input color data and threshold color data to determine if the titration reaction has reached its end-point. In another embodiment, the color processing device 10 is supplied with the threshold color data, and compares the color input data with the color threshold data and communicates the results to the controller 20. The color threshold data may be a range of RGB colors, into which RGB color data would fall if the titration has reached its end-point and the indicator has changed color. Accordingly, a different threshold color data may need to be supplied to varying reaction conditions, such as external lighting, as well as based on the indicator that is used.

If the end-point has been reached, the reactants of the titrand 8 have fully reacted because enough titrant 46 has been added to consume the reactant of the titrand 8. At this point, the indicator contained in the titrant/titrand mixture changes colors, and the color data reported to the controller 20 will be beyond the threshold color. In one embodiment, at the end-point of the titration the titrant/titrand mixture will turn from a purple/pink color to an amber/clear color.

In some embodiments, if the end-point has not been reached ("NO" on FIG. 5), wherein the controller 20 has determined that the input color data has not reached the threshold color, the dispenser 40 is instructed to continue to drop further volumetric amounts of titrant 46 into the titrant/titrand mixture, and continue the titrant addition step 102. If the titration end-point has been reached ("YES" on FIG. 5), wherein the controller 20 has determined that the input color data is past the threshold color, the process proceeds to a titration shut down step 108, wherein the controller 20 communicates to the dispenser 40 to not drop further titrant 46 into the titrant/titrand mixture in the container 2. Alternatively, the controller 20 may report the volume of titrant 46 contacted with the titrand 8 prior to the end-point of the titration, but may not necessarily stop the dispenser 40 from continuing to drop titrant 46 into the titrant/titrand mixture in container 2.

Following the titration shut down step 108, the volume of titrant 46 contacted with the titrand 8 over the course of the titration is reported in a reporting step 110. In one embodiment, the titrant 46 volume data may be visually shown on the display 32 for the user to view. In another embodiment the titrant 46 volume data may appear on the dispenser 40 and may be manually read by an operator. In another embodiment, the titrant 46 volume data may be determined by the number of drops dispensed from the dispenser 40 with the counter 56 and the volume of each drop dispensed by the dispenser 40.

Following the reporting step 110, the concentration of a component of the coating solution 80, such as the concentration of conversion coating material, is determined at step 112. A stochiometric calculation can be performed to determine the concentration, such calculation based on the reaction mechanism of the titrant 46 and titrand 8 reactants, volume of titrand 8 used in the titration, and volume of titrant 46 contacted with the titrand 8. The controller 20 may perform the calculation, or an operator may manually calculate the concentration of conversion coating material in the coating solution 80.

The automated titration device 1 and titration process presented herein allows for a standardized and consistent determination of a titration end-point. This determination may ensure that industrial processes, such as coating a metal component using a chemical bath of a selected concentration, are carried out in a satisfactory manner. The automated features of the device additionally allow for industrial operators to efficiently and accurately maintain process controls without expending excessive time and resources.

While the systems and methods have been described herein with specific reference to a conversion coating solution for an aluminum wheel, it should be understood that the systems and methods described herein may be used in conjunction with a variety of chemical compositions and components that are coated.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue. While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method for monitoring content of a coating solution for coating components, the method comprising:
   supplying a tank with the coating solution comprising a concentration of a solvent and a concentration of a coating material;
   testing the concentration of the coating material using a titration process, wherein the titration process comprises controllably contacting a volume of the coating solution with a reagent solution to form a mixture, using a color processing device to generate input color data based on the color of the mixture, and detecting an end-point of the titration process based on the input color data, wherein the input color data is RGB data and the end-point of the titration process is detected by comparing the input color data with threshold color data, wherein the threshold color data comprises an RGB triplet; and
   supplying one or both of the solvent and the coating material to the tank based on an amount of coating solution contacted with the reagent solution when an input color data signaling the end-point of the titration process is generated by the color processing device,
   wherein the threshold color data comprises a range of RGB triplets determined by at least one previously performed titration reaction.

2. The method for monitoring content of a coating solution of claim 1, wherein the color processing device is communicatively connected to a controller that receives the input color data and detects the end-point of the titration process.

3. The method for monitoring content of a coating solution of claim 2, wherein the controller determines the end-point of the titration process by comparing the input color data with threshold color data.

4. The method for monitoring content of a coating solution of claim 1, further comprising dispensing the coating solution into the reagent solution using a dispenser, the controller controlling the dispenser using an actuator.

5. The method for monitoring content of a coating solution of claim 4, further comprising monitoring the amount of coating solution contacted with the reagent solution using a counter.

6. The method for monitoring content of a coating solution of claim 1, wherein the titration process is a redox titration process.

7. The method for monitoring content of a coating solution of claim 1, wherein the coating solution increases corrosion resistance.

8. A method for monitoring content of a coating solution for coating components, the method comprising:
   supplying a tank with the coating solution comprising a concentration of a solvent and a concentration of a coating material;
   testing the concentration of the coating material using a titration process, wherein the titration process comprises:
      acquiring a sample of the coating solution from the tank and locating the sample of the coating solution in a dispenser;
      controllably dispensing the sample of the coating solution from the dispenser into a container holding an amount of a reagent solution using an actuator operably connected to the dispenser;
      generating input color data from a color processing device based on the color of the reagent solution with the coating solution added thereto, wherein the input color data is RGB color data; and
      comparing the input color data with threshold color data, wherein the threshold color data comprises an RGB triplet; and
   supplying one or both of the solvent and the coating material to the tank based, at least in part, on comparing the input color data with the threshold color data saved in memory,
   wherein the threshold color data comprises a range of RGB triplets determined by at least one previously performed titration reaction.

9. The method for monitoring content of a coating solution of claim 8, wherein the step of comparing the input color data with threshold color data is performed using a controller that is communicatively connected to the color processing device.

10. The method for monitoring content of a coating solution of claim 8, wherein the coating solution increases corrosion resistance.

11. The method for monitoring content of a coating solution of claim 8, further comprising monitoring the amount of coating solution contacted with the reagent solution using a counter.

12. The method for monitoring content of a coating solution of claim 8, wherein the coating solution and the reagent solution undergo a redox reaction when contacted.

13. A method for monitoring content of a coating solution for coating components, the method comprising:

maintaining a coating solution comprising a concentration of a solvent and a concentration of a coating material supplied to a tank by testing the concentration of the coating material using a titration process, wherein the titration process comprises controllably contacting a volume of the coating solution with a reagent solution to form a mixture, using a color processing device to generate input color data based on the color of the mixture, and detecting an end-point of the titration process based on the input color data, wherein the input color data is RGB data;

comparing the input color data with threshold color data to detect the end-point of the titration process, the threshold color data comprising an RGB triplet; and supplying one or both of the solvent and the coating material to the tank based on the amount of coating solution contacted with the reagent solution when the end-point of the titration process is detected, wherein the threshold color data comprises a range of RGB triplets determined by at least one previously performed titration reaction.

14. The method for monitoring content of a coating solution of claim 13, wherein the step of comparing the input color data with the threshold color data is performed using a controller.

15. The method for monitoring content of a coating solution of claim 13, further comprising monitoring the amount of coating solution contacted with the reagent solution using a counter.

16. The method for monitoring content of a coating solution of claim 13, wherein the coating solution and reagent solution undergo a redox reaction during the titration.

* * * * *